(12) United States Patent
Tsukahara et al.

(10) Patent No.: US 6,566,787 B2
(45) Date of Patent: May 20, 2003

(54) ELASTIC SURFACE-WAVE DEVICE

(75) Inventors: Yusuke Tsukahara, Tokyo (JP);
Kazushi Yamanaka, Sendai (JP);
Noritaka Nakaso, Tokyo (JP)

(73) Assignee: Toppan Printing Co., Ltd., Tokyo (JP)

( * ) Notice: Subject to any disclaimer, the term of this patent is extended or adjusted under 35 U.S.C. 154(b) by 0 days.

(21) Appl. No.: 09/930,959

(22) Filed: Aug. 17, 2001

(65) Prior Publication Data

US 2002/0014809 A1 Feb. 7, 2002

Related U.S. Application Data

(63) Continuation of application No. PCT/JP00/08961, filed on Dec. 18, 2000.

(30) Foreign Application Priority Data

Dec. 17, 1999 (JP) ............................................. 11-359312

(51) Int. Cl.[7] ............................................... H01L 41/08
(52) U.S. Cl. .................... 310/313 R; 310/369
(58) Field of Search ........................ 310/313 R, 313 A, 310/313 B, 367, 369

(56) References Cited

U.S. PATENT DOCUMENTS

| | | | | |
|---|---|---|---|---|
| 3,611,203 A | * | 10/1971 | Cooper et al. | 310/313 R |
| 3,786,373 A | * | 1/1974 | Schulz et al. | 310/313 R X |
| 3,815,056 A | * | 6/1974 | Meyer et al. | 310/313 R X |
| 3,878,477 A | * | 4/1975 | Dias et al. | 331/40 |
| 4,384,409 A | * | 5/1983 | Lao | 310/313 R X |
| 4,591,241 A | * | 5/1986 | Huignard | 310/313 R X |
| 6,164,135 A | * | 12/2000 | Bicz | 73/602 |

* cited by examiner

Primary Examiner—Mark O. Budd

(57) ABSTRACT

The present invention relates to an elastic surface-wave device, and more particularly to an elastic surface-wave device of a greatly increased performance, compared with a prior art elastic surface-wave device, and which is compact. The elastic surface-wave device includes a substrate including a surface having a region which is formed by at least a part of a spherical surface and is circularly continuous, and a surface acoustic wave generator which is provided in the surface region of the substrate and generates surface acoustic waves propagating in a continuous direction of the surface region. The surface acoustic wave generator generates surface acoustic waves in such a manner these waves can propagate only in the continuous direction without being diffused in a direction crossing the continuous direction along the surface region.

15 Claims, 4 Drawing Sheets

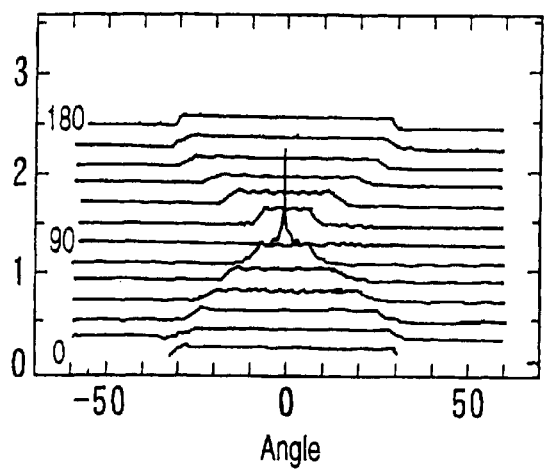
m = 600, half aperture angle $\theta_A$ = 30deg
FIG. 3A
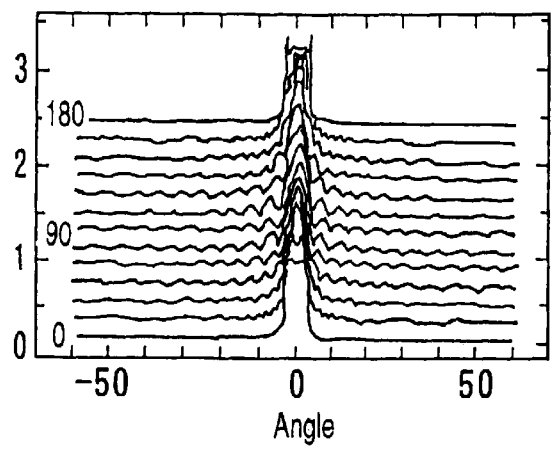
m = 600, half aperture angle $\theta_A$ = 3.5deg
FIG. 3B
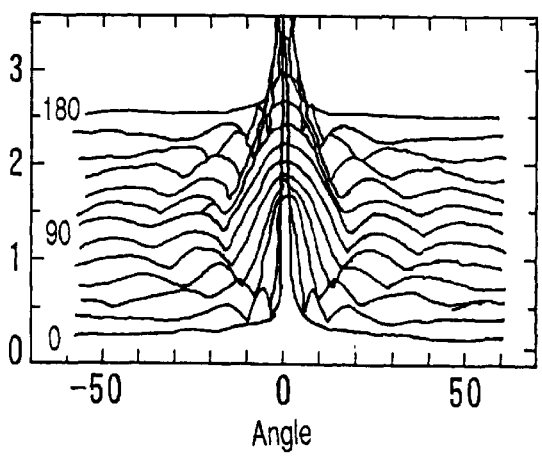
m = 600, half aperture angle $\theta_A$ = 1deg
FIG. 3C
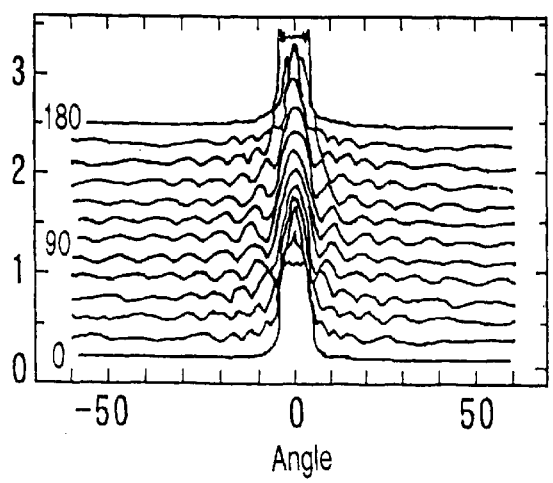
FIG. 3D    m = 300, half aperture angle $\theta_A$ = 4.5deg

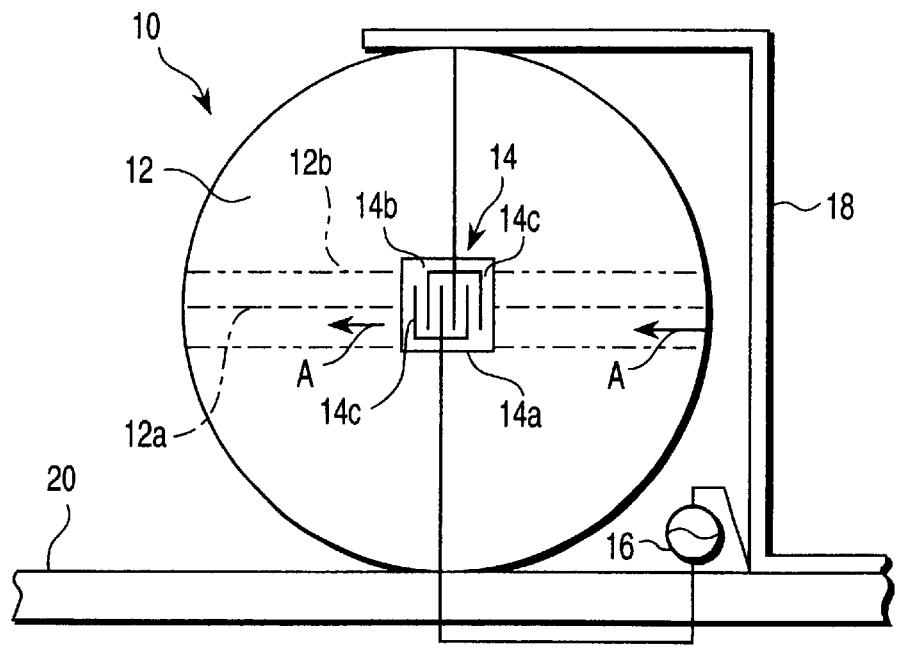
FIG. 4
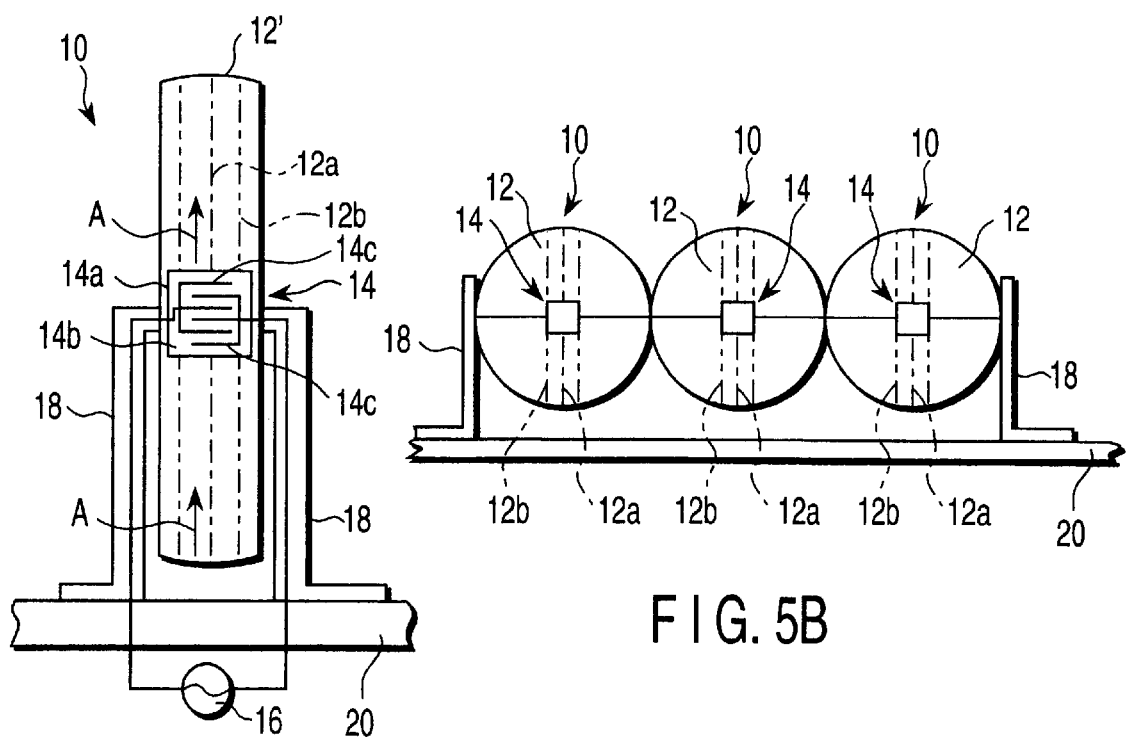
FIG. 5A
FIG. 5B

ELASTIC SURFACE-WAVE DEVICE

CROSS-REFERENCE TO RELATED APPLICATIONS

This is a Continuation Application of PCT Application No. PCT/JP00/08961, filed Dec. 18, 2000, which was not published under PCT Article 21(2) in English.

This application is based upon and claims the benefit of priority from the prior Japanese Patent Application No. 11-359312, filed Dec. 17, 1999, the entire contents of which are incorporated herein by reference.

BACKGROUND OF THE INVENTION

1. Field of the Invention

The present invention relates to an elastic surface-wave device comprising a substrate and a surface acoustic wave generator which is provided on a surface of the substrate and generates surface acoustic waves on the surface. More specifically, the present invention relates to a spherical elastic surface-wave device in which the substrate has a region being formed by at least a part of a spherical surface in the surface and circularly continuous, and the surface acoustic wave generator generates surface acoustic waves propagating in a direction along which the surface region of the substrate is continuous.

2. Description of the Related Art

An elastic surface-wave device which generates surface acoustic waves on a substrate and receives the surface acoustic waves generated on the substrate, is well known.

The surface acoustic wave is an elastic wave which intensively propagates almost all of its energy in a surface of a material, is different from a regular longitudinal wave or a transverse wave known as a bulk wave. As the surface acoustic wave, a Rayleigh wave, a Sezawa wave, a pseudo-Sezawa wave, a Love wave and others can be exemplified, and such waves can exist on a surface of an anisotropic substance.

In a conventional elastic surface-wave device, a pair of comb-like electrodes are provided on a flat piezoelectric material arranged on a flat substrate. When a high-frequency electric current is supplied to one comb-like electrode, surface acoustic waves are generated from the piezoelectric material in a direction along which one comb-like electrode is aligned on the substrate. The other comb-like electrode is arranged on the substrate in a moving direction of the surface acoustic waves generated from one comb-like electrode, and receives the surface acoustic waves.

The elastic surface-wave device is used for a delay line, an oscillation device and a resonance device for a transmitter, a filter for selecting a frequency, a chemical sensor, a biosensor, or a remote tag and the like.

A width of the surface acoustic waves in a direction orthogonal to a propagation direction of the surface acoustic waves generated by one of the pair of comb-like electrodes is generally equal to a length for which a plurality of electrode pieces of one comb-like electrode and a plurality of electrode pieces of the other comb-like electrode are opposed to each other. In the specification of the present application, this length is referred to as an electrode width.

In the elastic surface-wave device, in order to increase the accuracy of a resonance frequency of the surface acoustic wave transmitting between the pair of comb-like electrodes, it is desirable to reduce propagation losses which are generated when the surface acoustic waves are propagated between the pair of comb-like electrodes, as much as possible.

However, in the usual elastic surface-wave device, since the surface of the piezoelectric material to which the pair of comb-like electrodes are provided and the surface of the substrate are flat, the surface acoustic waves generated by one comb-like electrode are diffused in a direction orthogonal to the propagation direction of the surface acoustic waves on the surface and are weakened, when the surface acoustic waves are propagated on the flat surface toward the other comb-like electrode. Therefore, the propagation losses of the surface acoustic waves can not be reduced, and hence there is a limit to the increase of the performance in the elastic surface-wave device.

This invention is derived from the above-described problems, it is an object of the present invention to provide an elastic surface-wave device of greatly increased performance, compared with a prior art elastic surface-wave device, and which is compact.

BRIEF SUMMARY OF THE INVENTION

To achieve the above-mentioned object, an elastic surface-wave device according to the present invention, comprises: a substrate; and a surface acoustic wave generator which is provided on a surface of the substrate and generates surface acoustic waves on the surface, wherein the substrate has a region which is configured by at least a part of a spherical surface in the surface and circularly continuous, and wherein the elastic surface-wave generator is provided in the surface region of the substrate and generates surface acoustic waves in such a manner that the surface acoustic waves propagate along the surface region of the substrate only in a direction in which the surface region of the substrate is circularly continuous, without being diffused in a direction which crosses the continuous direction.

In the elastic surface-wave device according to the present invention and characterized by this configuration, the surface acoustic wave generator which is provided in the surface region of the substrate being configured by at least a part of a spherical surface and circularly continuous, generates surface acoustic waves so that the surface acoustic waves propagate in a direction in which the surface region of the substrate is circularly continuous on an outer surface of the substrate. Then, the surface acoustic waves propagate only in the continuous direction without being diffused in the crossing direction, along the surface region. Thus, the surface acoustic waves can propagate along the surface region without being diffused for a circumferential distance of the surface region, so that they can propagate infinitely.

Accordingly, a performance of the present invention can be greatly improved as compared with the conventional elastic surface-wave device. Further, since the substrate has in the surface thereof the surface region which is configured by at least a part of the spherical surface and circularly continuous, the device of the present invention can be compact.

In the elastic surface-wave device according to the present invention and characterized by being configured as described above, the substrate may be formed of a non-piezoelectric material. In this case, the surface acoustic wave generator includes: a piezoelectric material film provided in the surface region of the substrate; and an oscillator which is provided on a surface of the piezoelectric material film and generates surface acoustic waves in the continuous direction by applying an electric field to the piezoelectric material film.

The oscillator may include a comb-like electrode connected to a high-frequency power supply.

The substrate may be formed of a piezoelectric material. In this case, the surface acoustic wave generator may be provided with an oscillator which is provided in the surface region on the surface of the substrate and generates surface acoustic waves in the continuous direction by applying an electric field to the surface region of the substrate.

The oscillator may include a comb-like electrode connected to a high-frequency power supply.

When the oscillator includes the comb-like electrode connected to the high-frequency power supply, it is preferable that an arrangement cycle of a plurality of electrode pieces of the comb-like electrode is set to be not more than $\frac{1}{10}$ of a radius of the spherical surface of the substrate.

A wavelength of the surface acoustic waves generated by the oscillator is not a cycle of natural oscillation of the entire substrate but is substantially equal to the arrangement cycle of a plurality of the electrode pieces of the comb-like electrode.

When the oscillator includes the comb-like electrode connected to the high-frequency power supply, it is preferable that a length (electrode width) for which a plurality of the electrode pieces of the comb-like electrode are opposed to each other is set to be not more than a half of the diameter of the spherical surface of the substrate and not less than $\frac{1}{100}$ of the radius of the spherical surface.

A length of the comb-like electrode arranged in the surface region and an electric circuit pattern and the like attached thereto in a direction orthogonal to the continuous direction must be not more than a half of the circumferential length of the spherical surface of the substrate. Therefore, it is reasonable that a length (electrode width) for which a plurality of electrode pieces of the comb-like electrode are opposed to each other is not more than a half of the diameter of the spherical surface of the substrate. Further, when the length (electrode width) for which the electrode pieces are opposed to each other is not more than $\frac{1}{100}$ of the radius of the surface region of the substrate, the surface acoustic waves generated in the comb-like electrode are diffused in the direction orthogonal to the continuous direction while they are propagated in the continuous direction of the surface region. Then, when the surface acoustic waves diffused in the direction orthogonal to the continuous direction are inputted to the comb-like electrode, the comb-like electrode is influenced by an obstacle existing in a region in which the surface acoustic waves are diffused, and, for example, a frequency characteristic of the comb-like electrode may be possibly adversely affected.

In fact, it is preferable that a wavelength parameter (a circumferential length/a wavelength of surface acoustic waves in the continuous direction of the spherical surface) is 100 to 800 and a length (electrode width) for which a plurality of the electrode pieces of the comb-like electrode are opposed to each other in the orthogonal direction is equal to or more than a collimate angle (angle at which a collimated beam can be obtained).

It is preferable that the arrangement cycle of a plurality of the electrode pieces of the comb-like electrode is not more than $\frac{1}{10}$ of the radius of the spherical surface.

Moreover, it is preferable that each distance between a plurality of the electrode pieces of the comb-like electrode is not more than $\frac{1}{10}$ of the radius of the spherical surface.

In the present invention, the "substrate having a surface including a region which is formed by a part of a spherical surface and circularly continuous", of course, includes a substrate having a spherical shape and also includes a barreled substrate in which regions other than the above-described continuous region is cut off from the spherical shape, or a substantially disc-like substrate having a peripheral surface convexly curved toward the outside. In addition, a substrate having a spherical, barreled or substantially disc-like cavity is also included.

Therefore, the substrate may include a cavity including an inner surface having a region which is formed by at least a part of a spherical surface and circularly continuous, and an opening for causing the inside of the cavity to communicate with the outside of the substrate.

In such a case, the surface acoustic wave generator is provided in the continuous region of the inner surface of the cavity.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIGS. 3A, 3B, 3C and 3D are views schematically showing four states in which surface acoustic waves obtained by calculating an expression created by using the coordinate system in FIG. 2 and by changing a wave number parameter "m" (ratio of a wavelength of the surface acoustic waves to a circumferential length) a half of angular aperture, are propagated on the spherical substrate of the elastic surface-wave device;

FIG. 4 is a front view schematically showing a modification for electrically and structurally connecting and fixing the elastic surface-wave device according to the first embodiment in FIG. 1 to the substrate;

FIG. 5A is a front view schematically showing a modification of the elastic surface-wave device according to the first embodiment in FIG. 1, the modification being electrically and structurally connected and fixed on the substrate;

FIG. 5B is a front view schematically showing a plurality of elastic surface-wave devices each of which is according to the first embodiment in FIG. 1, the elastic surface-wave devices being electrically and structurally connected and fixed on the substrate.

DETAILED DESCRIPTION OF THE INVENTION

Figure 1:
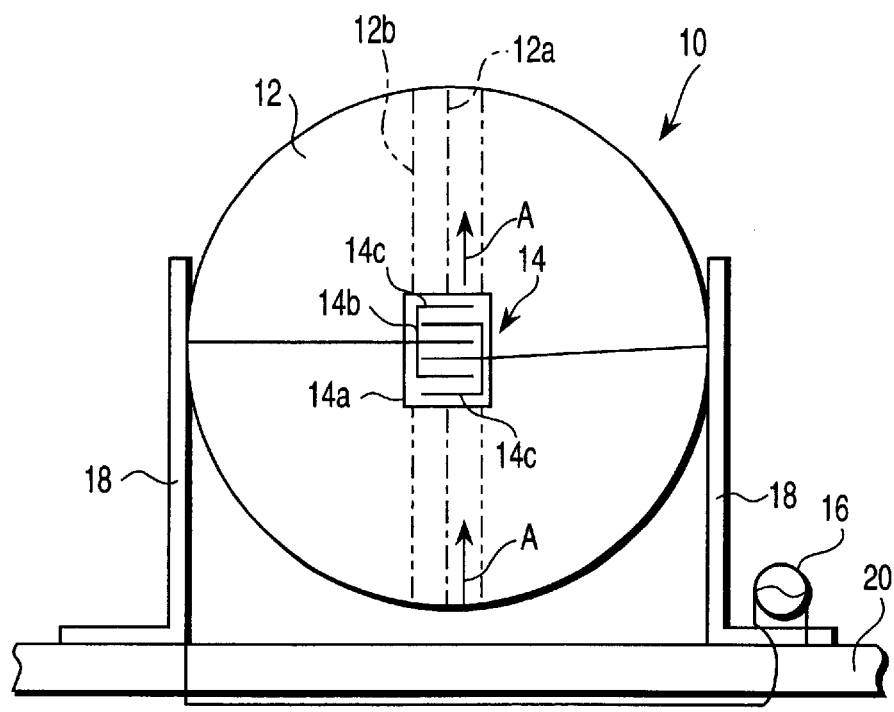
FIG. 1 is a front view schematically showing an elastic surface-wave device according to a first embodiment of the present invention and using a spherical substrate.

An elastic surface-wave device according to a first embodiment of the present invention will now be described in detail hereinafter with reference to FIG. 1 in the accompanying drawings.

The elastic surface-wave device 10 according to the first embodiment includes a spherical substrate 12, and a surface acoustic wave generator 14 set at a desired position on an outer surface of the substrate 12. The surface acoustic wave generator 14 generates surface acoustic waves which propagate as indicated by an arrow A along a maximum circumferential line 12a extending through the set position of the surface acoustic wave generator 14 in a direction in which a surface of the substrate 12 is continuous. The surface acoustic waves generated by the surface acoustic wave generator 14 propagate in a circular region 12b which is configured by at least a part of the spherical surface and circularly continuous along the maximum circumferential line 12a on the surface of the substrate 12, and are not diffused outside the circular region 12b in a direction orthogonal to the maximum circumferential line 12a extending in the continuous direction of the surface along the surface.

More specifically, the spherical substrate 12 is formed of a non-piezoelectric material, for example, glass or ceramic. The surface acoustic wave generator 14 includes a piezoelectric material film 14a attached at the desired position on the surface of the substrate 12, and an oscillator 14b which is provided on the piezoelectric material film 14a and generates the surface acoustic waves in the continuous direction. In this embodiment, the oscillator 14b has a comb-like electrode 14c connected to a high-frequency power supply 16. A plurality of electrode pieces of the comb-like electrode 14c are arranged in the continuous direction, and the both poles of the high-frequency power supply 16 are connected in opposite directions orthogonal to the maximum circumferential line 12a from the outside of the circular region 12b.

The spherical elastic surface-wave device 10 is supported by a pair of supports 18 fixed to the surface of the spherical substrate 12 outside the circular region 12b in opposite directions crossing the maximum circumferential line 12a so as to upwardly space the device from the substrate 20. A pair of supports 18 also function as conducting wires for electrically connecting a plurality of the electrode pieces of the comb-like electrode 14c with a predetermined electric circuit on the substrate 20, and the predetermined electric circuit is connected to both poles of the high-frequency power supply 16.

A wavelength of the surface acoustic waves generated from the elastic surface-wave generator 14 is set to be not more than 1/10 of a radius of the spherical surface of the substrate 12, and each distance between a plurality of the electrode pieces of the comb-like electrode 14c is therefore also set to be not more than 1/10 of the radius of the spherical surface of the substrate 12. Further, a width of the surface acoustic waves in the direction crossing the continuous direction along the surface is not more than the diameter of the spherical surface of the substrate 12 (more preferably, not more than a half of this diameter), and set to be not less than 1/100 of the radius. Therefore, a length (electrode width) for which a plurality of the electrode pieces of the comb-like electrode 14c are opposed to each other in the direction crossing the continuous direction along the surface is set to be not more than the diameter of the spherical substrate 12 (more preferably, not more than a half of the diameter) and not less than 1/100 of the radius.

Incidentally, the present invention was made by the present inventors of this application by discovering that, when surface acoustic waves are generated in a direction orthogonal to a circular arc in this circular arc in a predetermined range on the spherical surface, the surface acoustic waves propagate around on the spherical surface in the direction orthogonal to the circular arc without being diffused in the direction of the circular arc.

In regard to a generation source of the surface acoustic waves smaller than the predetermined range, assuming that the generation source of the surface acoustic waves is a point, for the sake of simplicity, the surface acoustic waves spread around the generation source in the form of concentric circles on the surface of the spherical substrate, and are then converged in the form of concentric circles toward a point on the opposed side of the generation source. Further, the surface acoustic waves spread again on the surface of the spherical substrate from the opposite side point, and are converged at the generation source of the surface acoustic waves provided at the position opposed to the opposite side point on the surface of the spherical substrate. That is, the surface acoustic waves emitted from the surface acoustic wave generation source smaller than the predetermined range, e.g., a generation source like a point, are disadvantageously diffused in a direction orthogonal to the propagating direction of the surface acoustic wave on the surface.

The surface acoustic waves generated from the surface acoustic wave generation source having a width wider than the predetermined range, propagate along a direction passing the center of the predetermined range and being orthogonal to a circular arc bridging over the predetermined range. In addition, the surface acoustic waves propagated as described above are converged on the spherical substrate toward a position corresponding to one pole when it is assumed that a circumferential line including the circular arc is an equator on the spherical substrate. Then, the surface acoustic waves having passed the position corresponding to the above described pole are diffused while the waves propagate toward another predetermined range which is the same as the former predetermined range on a directly opposite side of the former predetermined range on the circumferential line, and further converged toward a position corresponding to the other pole on the spherical substrate. After having passed the position corresponding to the other pole, the surface acoustic waves are again diffused when the waves propagate toward the former predetermined range. That is, the surface acoustic waves emitted from the surface acoustic wave generation source having the width wider than the predetermined range, repeat convergence and diffusion in each half part of the sphere.

In addition, a condition under which the surface acoustic waves propagate around on the spherical surface in the direction orthogonal to the circular arc without being diffused in the direction of the circular arc, was obtained as follows.

Figure 2:
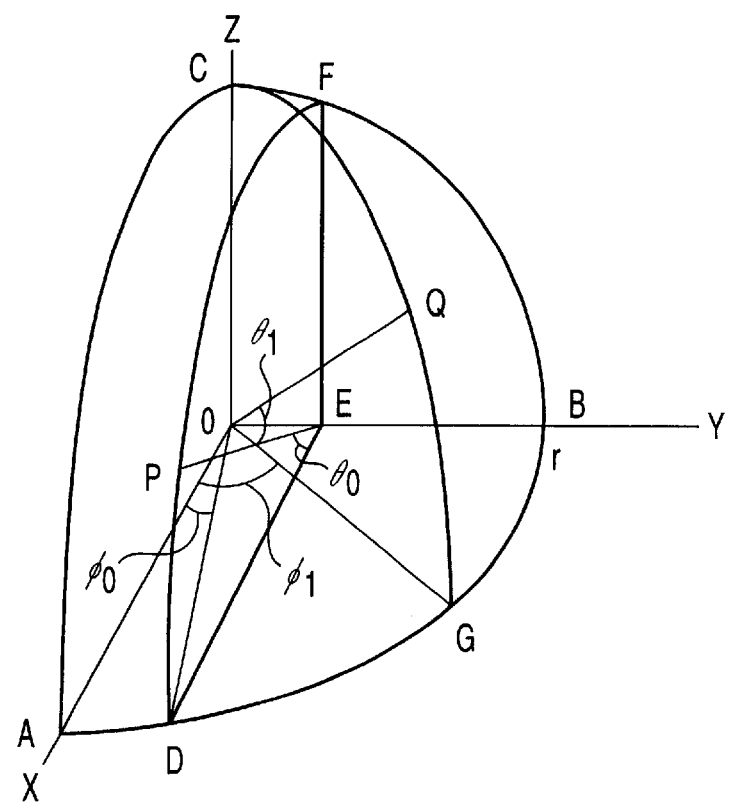
FIG. 2 shows a coordinate system which is a base for an expression used to specify a width for providing an oscillator at a predetermined position on an outer surface of a spherical substrate of the spherical elastic surface-wave device.

FIG. 2 shows a coordinate system for calculating technical advantages of the present invention. In the coordinate system, intersection points of coordinate axes x, y, z with a spherical surface having a radius r are designated as A, B and C, and surface acoustic waves generated from a point P on a circular arc DF parallel to a circular arc AC reach a point Q on a circular arc CG. When taking angles $\phi_0$, $\theta_0$, $\phi_1$ and $\theta_1$ as shown in FIG. 2, the coordinates of the points P and Q are:

($r\cos\phi_0 \cos\theta_0$, $r\sin\phi_0$, $r\cos\phi_0 \sin\theta_0$); and ($r\cos\phi_1 \cos\theta_1$, $r\cos\theta_1 \sin\phi_1$, $r\sin\theta_1$).

Therefore, the following expression can be obtained:

$$PQ^2 = 2r^2[1 - \cos\phi_0 \cos\theta_0 \cos\phi_1 \cos\theta_1 - \sin\phi_0 \cos\phi_1 \cos\theta_1 - \cos\phi_0 \sin\phi_0 \sin\theta_1] \quad (1).$$

Accordingly, assuming that the angle POQ=θ, from the theorem of cosines, the following relationship can be attained:

$$\cos\theta = \cos\phi_0 \cos\theta_0 \cos\phi_1 \cos\theta_1 + \sin\phi_0 \cos\phi_1 \cos\theta_1 + \cos\phi_0 \sin\phi_0 \sin\theta_1 \quad (2).$$

The component of the particle displacement of the surface acoustic waves generated at the point P, in the radial direction at the point Q is represented by the following expression (Viktorov, Rayleigh and Lamb Waves):

$$u_r = R_e\left[\frac{C}{\sqrt{\sin\theta}} \exp\left\{im\left(\theta - \frac{C_R t}{r}\right)\right\}\right] \quad (3)$$

wherein "C" is a constant, and "m" is a ratio of a wave length of the surface acoustic waves to a circumferential length, which is referred to as a wave number parameter. Further, $C_R$ is a velocity of Rayleigh wave, and t is a time. The angle θ can be obtained from the expression (2). A sound field of the point Q by a circular arc sound source having an angle 2θA seen from the point E can be obtained by integrating the expression (3) with respect to $\theta_0$ from $-\theta_A$ to $\theta_A$. The distribution of the sound field can be obtained through a calculation while changing an angle of elevation $\theta_1$ of the point Q.

FIGS. 3A, 3B, 3C and 3D show four states in which the surface acoustic waves obtained by using the expression (3) are propagated on the spherical substrate 12 in case of $\phi_0=0$ where the point P is positioned on the X–Z plane.

FIGS. 3A, 3B and 3C show results of examining the sound filed in the case of the wave number parameter m=600 (dependence of an absolute value of the particle displacement with respect to the angle $\theta_1$). In the respective figures, the lowermost plot shows the sound field in the case where an angle (propagation angle) $\phi_1$ representing propagation of the surface acoustic waves on the spherical surface is 10°, and the sound fields obtained by increasing the angle in increments of 20° in the ascending manner are sequentially plotted.

FIG. 3A shows the case of a half aperture angle $\theta_A=30°$. In this case, as apparent from FIG. 3A, the propagation state of the surface acoustic waves is a converged beam shape. That is, as the propagation angle $\phi_1$ is increased, the width of the sound field is decreased. After the width of the sound field becomes minimum with $\phi_1=90°$, the width is again increased, and the same distribution as that on the sound source is recreated with the antipole point of 180°. Thereafter, the same change is repeated every 180°, and the same change is repeated even if the surface acoustic waves propagate around again and again. This is a phenomenon peculiar to the spherical surface on which there is no diffusion of the waves by the diffraction. In this case, the sound field does not become wider than the half aperture angle $\theta_A=30°$, and the energy of the surface acoustic waves is confined in a zonary portion of $\theta_1<\theta_A$. In this case, even if any other material is brought into contact with the portion of $\theta_1<\theta_A$ on the outer surface of the spherical substrate 12, disturbance is not generated in the sound field.

FIG. 3C shows the case of the half aperture angle of $\theta_A=1°$. In this case, as apparent from FIG. 3C, the surface acoustic waves are propagated in the form of divergent beams similar to that in the point sound source. That is, as the propagation angle $\phi_1$ increases, the width of the sound field also increases. After the width of the sound field becomes maximum with $\phi_1=90°$, the width is again decreased, and the same distribution as that on the sound source is recreated with the antipole point of 180°. In this case, different from the case of the converged beam mentioned with reference to FIG. 3A, the energy of the surface acoustic waves is not confined in the zonary portion of $\theta_1<\theta_A$ but spreads on the entire spherical surface with $\phi_1=90°$. In such a case, when any other material is brought into contact with the portion of $\theta_1>\theta_A$ on the outer surface of the spherical substrate 12 with $\phi_1=90°$ on the outer surface of the spherical substrate 12, disturbance occurs in the sound field.

FIG. 3B shows the case of the half aperture angle $\theta_A=3.5°$. In this case, as apparent from FIG. 3B, the surface acoustic waves are propagated in the form of collimated beams that the width of the sound field does not substantially change even if the propagation angle $\phi_1$ increases. That is, the energy of the surface acoustic waves is confined in a zonary portion of $\theta_1=\theta_A$. This is the characteristic similar to the Bessel beam in an infinite medium. Further, the half aperture angle $\theta_A$ at which the collimated beam can be obtained is referred to as a collimating angle $\theta_{col}$.

As apparent from FIGS. 3A to 3C, when the half aperture angle $\theta_A$ is substantially equal to the collimating angle $\theta_{col}$, the energy of the surface acoustic waves is confined to the zonary portion having a narrowest width.

Furthermore, as a result of performing a numerical analysis similar to that described above by changing the wave number parameter, it was found that the collimating angle $\theta_{col}$ is changed by the wave number parameter "m". FIG. 3D shows that the surface acoustic waves are propagated in the form of the collimated beam with the wave number parameter "m" of 300 when the half aperture angle $\theta_A$ is substantially 4.5°. In this case, the collimating angle $\theta_{col}$ is approximately 4.5°.

The following shows values of the collimating angle $\theta_{col}$ when the wave number parameter "m" varies.

Wave number parameter "m" Collimating angle $\theta_{col}$

| Wave number parameter "m" | Collimating angle $\theta_{col}$ |
| --- | --- |
| 150 | 7.0 |
| 300 | 4.5 |
| 450 | 4.0 |
| 600 | 3.5 |
| 750 | 3.0 | wherein "m" is circumferential length of the sphere/wavelength of the surface acoustic waves.

These are approximate values obtained by numerical calculation.

As apparent from the above detailed description, in this embodiment, the collimating angle $\theta_{col}$ is obtained from the wave number parameter "m" by using the above expression (3). And, it is assumed that the elastic surface-wave generator 14, or more specifically, the comb-like electrode 14c of the oscillator 14b of the elastic surface-wave generator 14, is provided at a desired position on the surface of the spherical material 12 so as to be wider than the width defined by the collimating angle $\theta_{col}$, and the surface acoustic waves are generated by the elastic surface-wave generator 14. In this case, the surface acoustic waves are propagated in the range defined by a length (electrode width) for which a plurality of the electrode pieces of the comb-like electrode 14c are opposed to each other, on the outer surface of the spherical substrate 12 without being diffused in the direction of the collimating angle $\theta_{col}$. In FIG. 1, the range defined by the electrode width corresponds to the circular region 12b, and the direction orthogonal to the collimating angle $\theta_{col}$ corresponds to the direction along the maximum circumferential line 12a.

FIG. 4 schematically shows a modification of the structure for providing the elastic surface-wave device 10 of the first embodiment according to the present invention mentioned in connection with FIG. 1, at a predetermined position on the substrate 20.

In this modification, an outer end of one of a pair of the conducting wires for the comb-like electrode 14e extended to the outside of the circular region 12b in the direction crossing the maximum circumferential line 12a on the surface of the spherical substrate 12 of the elastic surface-wave device 10 is electrically and structurally connected and fixed to a predetermined position of the electric circuit on the substrate 20. In addition, an outer end of the other one of a pair of the conducting wires is connected to an extending end of a support post which is electrically and structurally connected to a predetermined position of the electric circuit on the substrate 20.

As described above, any region of the spherical surface of the elastic surface-wave device 10 according to the present invention can be used for connecting or fixing the elastic surface-wave device 10 on the substrate 20, excepting the circular region 12b in which the surface acoustic waves are propagated.

Thus, as shown in FIG. 5A, the spherical substrate 12 can be configured into a flat discoid shape by eliminating regions other than the circular region 12b. The circumferential surface of a discoid substrate 12' constitutes the circular region 12b, and the circumferential surface of the circular region 12b is configured by a part of the spherical surface which is convex toward the outside and circularly continuous.

Additionally, as shown in FIG. 5B, a plurality of the elastic surface-wave devices 10 can be connected to each other in any region other than the circular region 12b.

The present invention does not exclude provision of a plurality of the elastic surface-wave generators 14 on the surface of the same spherical substrate 12. In this case, a plurality of the elastic surface-wave generators 14 must be arranged on the surface of the same spherical substrate 12 in such a manner that the propagation paths of the surface acoustic waves generated by the surface acoustic wave generators 14 are not overlap each other.

Also, the present invention does not exclude the case where a plurality of arrangement intervals of multiple electrode pieces of the comb-like electrode 14 exist or the case where the arrangement interval is continuously changed. Further, the present invention does not exclude the case where a plurality of the electrode pieces include some electrode pieces having the arrangement intervals which do not largely contribute (or which are not intended to contribute) to output of the surface acoustic waves from the elastic surface-wave generator 14.

The oscillator for applying the electric field to the piezoelectric material film may be arranged between the piezoelectric material film and the substrate or arranged on the surface opposed to the substrate in the piezoelectric material film.

Furthermore, the oscillator does not have to be in direct contact with the piezoelectric material film or the substrate of the piezoelectric material. For example, if the oscillator has the comb-like electrode, it is good enough that the comb-like electrode is located near to the surface of the substrate and is fixed relatively to the substrate within 1/10 of the arrangement cycle of a plurality of electrode pieces of the comb-like electrode.

Incidentally, the elastic surface-wave device 10 is formed by providing oscillating means 14b on the piezoelectric material film 14a provided at a predetermined position of the outer surface of the spherical substrate 12 of the non-piezoelectric material in the above-described embodiment and modification. However, when the substrate 12 is formed by the piezoelectric material, the oscillator 14b can be directly provided at a predetermined position on the outer surface of the substrate 12 formed by the piezoelectric material.

Figure 6:
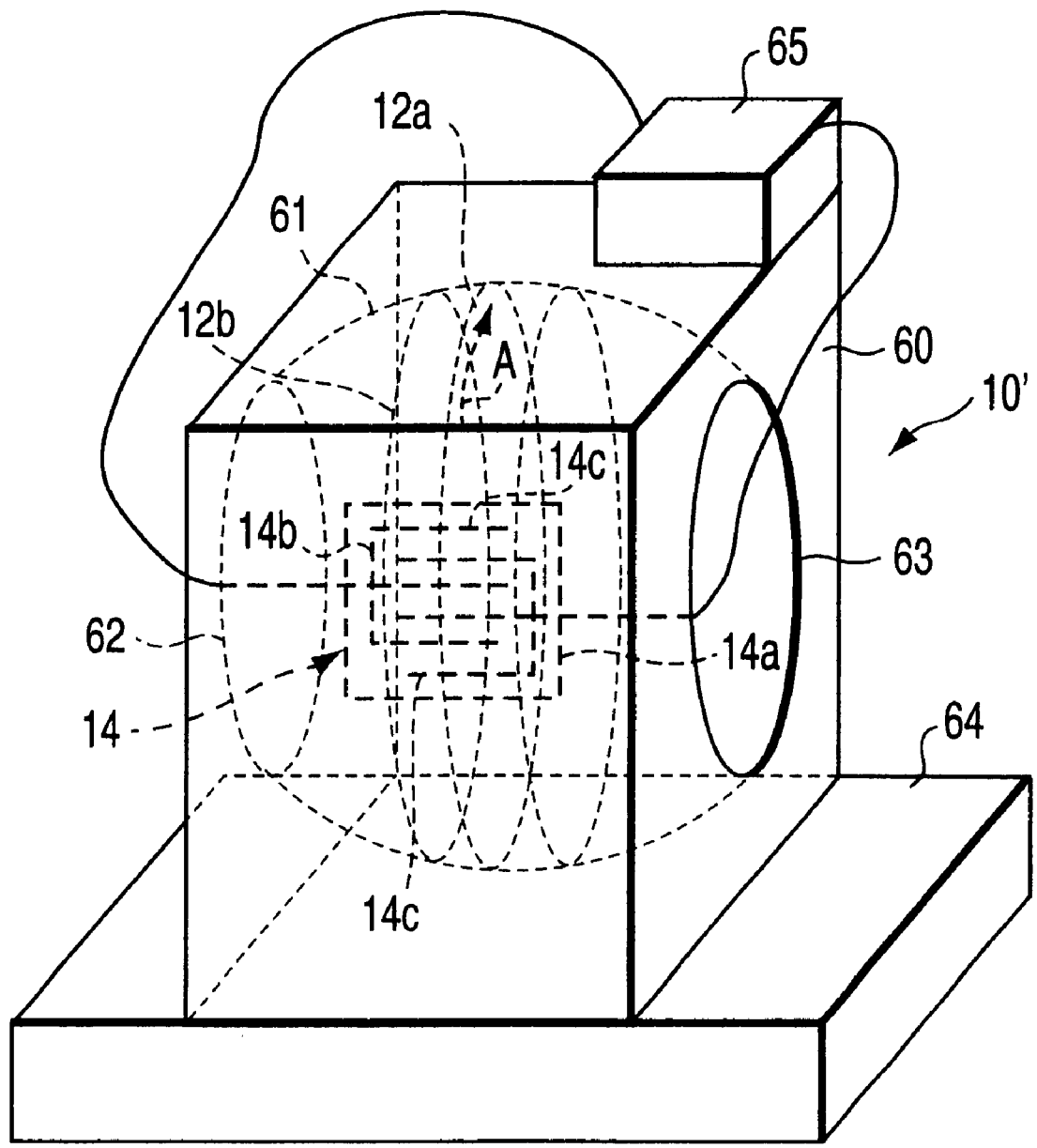
FIG. 6 is a perspective view schematically showing an elastic surface-wave device according to a second embodiment of the present invention and using a substrate having a spherical cavity.

FIG. 6 is a schematic perspective view showing an elastic surface-wave device 10' according to a second embodiment of the present invention, which uses a substrate 60 including a barreled cavity 61 having an inner surface including a region 12c which is formed by at least a part of the spherical surface and circularly continuous. At the area on the inner surface of the cavity 61, a surface acoustic wave generator 14 is provided. The cavity 61 communicates with the outside space through a pair of outside communication openings 62 and 63 opposed to each other in the cavity 61. A pair of conducting wires for a pair of comb-like electrodes 14c of an oscillator 14b of the surface acoustic wave generator 14 are led from a pair of the comb-like electrodes 14c in the cavity 61 to a high-frequency power supply 65 on the outer surface of the substrate 60 through a pair of the outside communication openings 62 and 63. The substrate 60 can be supported on a support 64.

In this case, when an electric field is applied to a pair of the comb-like electrodes 14c by the high-frequency power supply 65, the elastic surface-wave device 10' operates as similar to the elastic surface-wave generator 10 of the first embodiment or its various modifications according to the present invention described with reference to FIGS. 1 to 5B. That is, the surface acoustic wave generator 14 generates surface acoustic waves which propagate as indicated by an arrow A along a maximum circumferential line 12a which is continuously extending in a direction passing a set position of the surface acoustic wave generator 14 on the inner surface of the cavity 61. The surface acoustic waves generated by the surface acoustic wave generator 14 of the elastic surface-wave device 10' propagate in the circular region 12b which is configured by at least a part of the spherical surface and circularly continuous along the maximum circumferential line 12a on the inner surface of the cavity 61 of the substrate 60. Furthermore, the surface acoustic waves infinitely propagate around along the inner surface without being diffused toward the outside of the circular region 12b in a direction crossing the maximum circumferential line 12a which is in a continuous direction of the inner surface.

Moreover, in the elastic surface-wave device 10' according to the second embodiment, when a fluid such as a gas or a liquid is flown in the cavity 61 through a pair of the outside communication openings 62 and 63 of the substrate 60, it is possible to facilitate a use of the elastic surface-wave device 10' as a chemical sensor or a biosensor for that fluid.

In addition, there is no limit to the diameter of the outer surface or the inner surface of the substrate which is formed by at least a part of the spherical surface used in the elastic surface-wave device according to the present invention and is circularly continuous. A variety of diameters from very large to very small can be prepared by all the currently known methods.

Additionally, the piezoelectric material film provided at a predetermined position on the outer surface or the inner surface of the substrate can be prepared by all the currently known methods, and the oscillator provided at a predetermined position on the piezoelectric material film, on the outer surface of the substrate formed by the piezoelectric material or on the inner surface of the cavity of the substrate can be also prepared by all the currently known methods. All the currently known methods described herein include attaching the comb-like electrode which is prepared by independently forming a conductive foil to a comb-like electrode shape, onto a predetermined position on the piezoelectric material film or on the outer surface of the substrate formed by the piezoelectric material or on the inner surface of the cavity of the substrate, or independently forming the conductive material into the comb-like electrode shape by deposition, printing, sputtering, or the like on the piezoelectric material film or on the outer surface of the substrate formed by the piezoelectric material or on the inner surface of the substrate.

Additionally, in a case that the substrate is configured by using an elastic anisotropic material, the wavelength of the surface acoustic waves generated by the surface acoustic wave generator is changed in accordance with a position where the surface acoustic wave generator is set on the surface of the substrate.

As is apparent from the above detailed description, the elastic surface-wave device according to the present invention can be used for a delay line, an oscillation device and a resonance device for a transmitter, a filter for selecting a frequency, a chemical sensor, a biosensor, a remote tag and others.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An elastic surface-wave device comprising:
   a substrate having a surface, where the surface comprises a circularly continuous band on a spherical shape and the circularly continuous band is continuous in a first direction, and
   a surface acoustic wave generator which is provided on the surface of the substrate at the circularly continuous band and generates surface acoustic waves on the surface,
   wherein the spherical shape is related to the surface acoustic wave so that the surface acoustic wave propagates within the circularly continuous band in the first direction without diffusing over the circularly continuous band in a second direction other than the first direction.

2. An elastic surface-wave device according to claim 1, wherein the substrate is formed of a non-piezoelectric material; and
   wherein the surface acoustic wave generator includes a piezoelectric material film provided at the surface, and an oscillator which is provided on a surface of the piezoelectric material film and generates surface acoustic waves in the first direction by applying an electric field to the piezoelectric material film.

3. An elastic surface-wave device according to claim 2, wherein the oscillator includes a comb-like electrode connected to a high-frequency power supply.

4. An elastic surface-wave device according to claim 1, wherein the substrate is formed of a piezoelectric material; and
   wherein the surface acoustic wave generator includes an oscillator which is provided at the surface and generates the surface acoustic waves in the first direction by applying an electric field to the surface of the substrate.

5. An elastic surface-wave device according to claim 4, wherein the oscillator includes a comb-like electrode connected to a high-frequency power supply.

6. An elastic surface-wave device comprising a substrate, and a surface acoustic wave generator which is provided on a surface of the substrate and generates surface acoustic waves on the surface,
   wherein the substrate has a surface region which is configured by at least a part of a spherical surface in the surface and is circularly continuous;
   wherein the elastic surface-wave generator is provided in the surface region of the substrate and generates surface acoustic waves in such a manner that the surface acoustic waves propagate within the surface region of the substrate in a direction in which the surface region of the substrate is circularly continuous, without being diffused over the surface region in a direction which crosses the continuous direction, and
   wherein a wavelength of the surface acoustic waves is set to be not more than $\frac{1}{10}$ of a radius of the spherical surface of the substrate.

7. An elastic surface-wave device comprising a substrate, and a surface acoustic wave generator which is provided on a surface of the substrate and generates surface acoustic waves on the surface,
   wherein the substrate has a surface region which is configured by at least a part of a spherical surface in the surface and is circularly continuous;
   wherein the elastic surface-wave generator is provided in the surface region of the substrate and generates surface acoustic waves in such a manner that the surface acoustic waves propagate within the surface raglan of the substrate In a direction in which the surface region of the substrate is circularly continuous, without being diffused over the surface region in a direction which crosses the continuous direction, and
   wherein a width of the surface acoustic waves in a direction crossing the continuous direction along the surface of the substrate is set to be not more than one half of a diameter of the spherical surface of the substrate and not less than $\frac{1}{100}$ of a radius of the spherical surface.

8. An elastic surface-wave device comprising a substrate, and a surface acoustic wave generator which is provided on a surface of the substrate and generates surface acoustic waves on the surface,
   wherein the substrate has a surface region which is configured by at least a part of a spherical surface in the surface and is circularly continuous;
   wherein the elastic surface-wave generator is provided in the surface region of the substrate and generates surface acoustic waves in such a manner that the surface acoustic waves propagate within the surface region of the substrate in a direction in which the surface region of the substrate is circularly continuous, without being diffused over the surface region in a direction which crosses the continuous direction, and
   wherein the oscillator includes a comb-like electrode connected to a high-frequency power supply, and
   wherein an arrangement cycle of a plurality of electrode pieces of the comb-like electrode is set to be not more than $\frac{1}{10}$ of a radius of the spherical surface of the substrate.

9. An elastic surface-wave device comprising a substrate, and a surface acoustic wave generator which is provided on a surface of the substrate and generates surface acoustic waves on the surface, wherein the substrate has a surface region which is configured by at least a part of a spherical surface in the surface and is circularly continuous;

wherein the elastic surface-wave generator is provided in the surface region of the substrate and generates surface acoustic waves in such a manner that the surface acoustic waves propagate within the surface region of the substrate in a direction in which the surface region of the substrate is circularly continuous, without being diffused over the surface region in a direction which crosses the continuous direction, and wherein the Oscillator includes a comb-like electrode connected to a high-frequency power supply, and wherein a length for which a plurality of electrode pieces of the comb-like electrode are opposed to each other is set to be not more than one half of a diameter of the spherical surface of the substrate and not less than 1/100 of a radius of the spherical surface.

10. An elastic surface-wave device according to claim 3, wherein an arrangement cycle of a plurality of electrode pieces of the comb-like electrode is not more than 1/10 of a radius of the spherical shape.

11. An elastic surface-wave device according to claim 5, wherein each distance between a plurality of electrode pieces of the comb-like electrode is not more than 1/10 of a radius of the spherical shape.

12. An elastic surface-wave device according to claim 1, wherein:

the substrate includes a cavity and openings for causing the inside of the cavity to communicate with the outside of the substrate, and an inner surface of the substrate facing the cavity includes the surface which is circularly continuous.

13. An elastic surface-wave device according to claim 1, wherein:

the substrate comprises a spherical surface having the spherical shape, and the acoustic waves do not diffuse through the portions of the spherical surface outside of the circularly continuous band.

14. An elastic surface-wave device according to claim 1, wherein a wavelength of the surface acoustic waves is related to a radius of the spherical shape such that the generated surface acoustic waves propagate in the first direction without diffusing in the second direction.

15. An elastic surface-wave device according to claim 1, wherein the surface acoustic wave generator generates the surface acoustic waves having a width in a direction orthogonal to the first direction, and the width is related to a radius of the spherical shape such that the generated surface acoustic waves propagate in the first direction without diffusing in the second direction.

* * * * *

UNITED STATES PATENT AND TRADEMARK OFFICE
CERTIFICATE OF CORRECTION

PATENT NO. : 6,566,787 B2 Page 1 of 1
APPLICATION NO. : 09/930959
DATED : May 20, 2003
INVENTOR(S) : Yusuke Tsukahara et al.

It is certified that error appears in the above-identified patent and that said Letters Patent is hereby corrected as shown below:

On the front cover page, under the (73) Assignee section:
insert --Kazushi Yamanaka, Sendai-shi (JP)--

Signed and Sealed this

Thirteenth Day of July, 2010

David J. Kappos
*Director of the United States Patent and Trademark Office*